United States Patent [19]

Cecere et al.

[11] Patent Number: 4,504,303
[45] Date of Patent: Mar. 12, 1985

[54] DERIVATIVES OF AZOLES HAVING PHYTOGROWTH REGULATING ACTIVITY

[75] Inventors: Mirella Cecere; Franco Gozzo, both of Milan; Ernesto Signorini, Varese, all of Italy

[73] Assignee: Montedison S.p.A., Milan, Italy

[21] Appl. No.: 475,974

[22] Filed: Mar. 16, 1983

[30] Foreign Application Priority Data

Mar. 19, 1982 [IT] Italy ............................. 20271 A/82

[51] Int. Cl.³ .................. A01N 43/50; A01N 43/64; C07D 233/60; C07D 249/08
[52] U.S. Cl. ................................. 71/76; 71/92; 548/262; 548/341; 548/378; 548/561; 548/562
[58] Field of Search ............ 548/262, 341; 71/92, 71/76

[56] References Cited

U.S. PATENT DOCUMENTS 4,079,143  3/1978  Balasubramanyam et al. ..... 548/262

FOREIGN PATENT DOCUMENTS 2908323  9/1980  Fed. Rep. of Germany ...... 424/269

OTHER PUBLICATIONS

Cecere et al., Chem. Abstracts, vol. 100, Abstract No. 68305s (1983), (Abstract of German OlS 3,309,870, Sep. 29, 1983, Claiming Priority of It. 82/20271).

*Primary Examiner*—Alton D. Rollins

[57] ABSTRACT

There are disclosed derivatives of five-membered nitrogen-containing heterocycles substituted on the nitrogen atom in position 1 by polyfunctional alkenyl groups. Said compounds are endowed with phytogrowth-regulating activity and, in higher doses, with herbicidal activity. A process for synthesizing the compounds and their use in agriculture are also disclosed.

9 Claims, No Drawings

DERIVATIVES OF AZOLES HAVING PHYTOGROWTH REGULATING ACTIVITY

This invention relates to new derivatives of nitrogen-containing heterocycles and more particularly it relates to five-membered nitrogen-containing heterocycles substituted on the nitrogen atom in position 1 by polyfunctional alkenyl groups, which are endowed with phytogrowth regulating and herbicide activities.

Furthermore, the invention relates to a process for synthesizing the compounds of the invention and to their use in agriculture.

According to the present invention there are provided compounds of the general formula

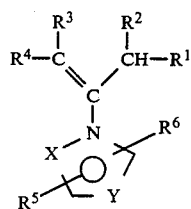

in which:

X and Y (equal to or different from each other) represent a nitrogen atom or a CH group;

$R^1$ and $R^2$ (equal to or different from each other) represent

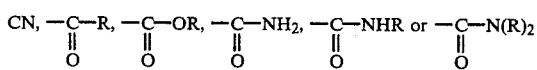

wherein R represents an alkyl group having 1 to 4 carbon atoms or a phenyl group which may be substituted by one or more halogen atoms, an alkyl group having 1 to 4 carbon atoms or an alkoxyl group having 1 to 4 carbon atoms;

$R^3$ and $R^4$ (equal to or different from each other) represent a hydrogen atom, a chlorine or bromine atom, an alkyl group having 1 to 5 carbon atoms, an alkenyl group having 2 to 6 carbon atoms which may be substituted by one or more halogen atoms, a phenyl group which may be substituted by one or more halogen atoms, an alkyl group having 1 to 4 carbon atoms or an alkoxyl group having 1 to 4 carbon atoms;

$R^5$ and $R^6$ (equal to or different from each other) represent a hydrogen atom, a halogen, an alkyl group having 1 to 5 carbon atoms which may be substituted by 1 to 3 halogen atoms.

The compounds of general formula I are endowed with phytogrowth regulating activity.

The chemical name of the compounds of formula I varies depending on the different meanings of the substituents since these represent functional groups which characterize the molecule according to the chemical nomenclature.

For example, in the simplest case, in which the substituents $R^3$ and $R^4$ are both hydrogen atoms and R is an alkyl group, if one of the substituents $R^1$ and $R^2$ is a COOR or CONH$_2$ group and the other substituent is a —CO—R group, the compounds of formula I are considered as esters or amides of 3-butenoic acid, which are substituted in position 2 by an alkyl-carbonyl group and in position 3 by one of the heterocyclic groups comprised among those encompassed in the general formula.

Likewise, when both groups $R^1$ and $R^2$ are COOR or CONH$_2$, the compounds of formula I are still to be considered as derivatives of 3-butenoic acid, in this case substituted in position 2 by an alkoxy-carbonyl or amino-carbonyl group and in position 3 by a heterocyclic group. When both groups $R^1$ and $R^2$ are —CO—R groups, the compounds of formula I are considered as derivatives of an alkyl-allyl-ketone, where the allyl radical is substituted in position 1 by an alkyl-carbonyl group and in position 2 by one of the heterocyclic groups comprised among those considered in the general formula.

Examples of heterocyclic radicals considered in the general formula are: 1-imidazolyl (X=CH, Y=N), 1-pyrazolyl (X=N, Y=CH) and 1-(1,2,4,-triazolyl) (X=N, Y=N).

When substituents $R^3$ and $R^4$ are different from hydrogen atoms and substituent R is different from an alkyl group, the chemical name of the compounds of formula I will consequently be different.

Synthesis of the compounds of formula I is carried out by reacting a heterocyclic compound of formula

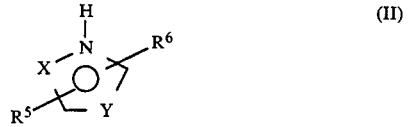

[in which X, Y, $R^5$ and $R^6$ have the same meanings as in formula (I)] with an unsaturated compound having the formula

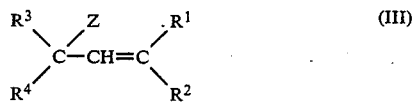

[in which $R^1$, $R^2$, $R^3$ and $R^4$ have the same meanings as in formula (I) and Z=Cl, Br] and subsequent elimination of a molecule of hydrogen halide (HZ).

When the heterocyclic compound II is a triazole derivative, the addition intermediate can be isolated before elimination of the hydrogen halide.

Such intermediate, of formula

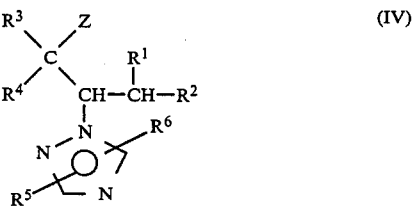

(in which $R^1$, $R^2$, $R^3$, $R^4$, $R^5$, $R^6$ and Z have the meanings stated) is then dehydrohalogenated by treatment with a suitable base.

On the contrary, when the nucleus of the heterocyclic compound II is of imidazole, the compounds of formula I are obtained directly.

Our tests of the intermediates of formula IV did not show any activity as phytogrowth regulators.

A general procedure for the synthesis of the compounds of formula I consists in reacting the heterocyclic compound II with the unsaturated compound III in the presence of an at least stoichiometric amount of an organic or inorganic base in a suitable inert solvent.

A tertiary amine, for example triethylamine, may be used as organic base, and this, when in excess, may act as the reaction medium.

An alkali hydroxide or carbonate, particularly potassium hydroxide, can be used as inorganic base, and in this case the presence of a polar solvent, as reaction medium, becomes necessary.

Generally the reaction proceeds at room temperature and the heat produced may be absorbed according to the normal techniques of thermal exchange. The reaction temperature is not a critical factor, but in the syntheses carried out by use, it was maintained at values comprised between room temperature and 60° C.

The progress of the reaction can be controlled by observing the disappearance of compound III from the reaction medium. When the reaction is finished, the mixture is treated according to the usual techniques and the product of formula I can be purified by crystallization from a suitable solvent or by means of column chromatography.

If intermediates of formula IV are to be isolated, it is sufficient to react the triazole of formula II with the unsaturated compound of formula III in the presence of catalytic amounts of a base. The compounds of formula I, wherein at least one of the substituents $R^1$ and $R^2$ is a —CO—R group, can exist in different tautomeric forms, as a consequence of the well-known capacity of the ketones to assume the enolic form. The NMR analysis of said compounds shows that they essentially exist in the enolic form (I-A), when they are dissolved in $CDCl_3$.

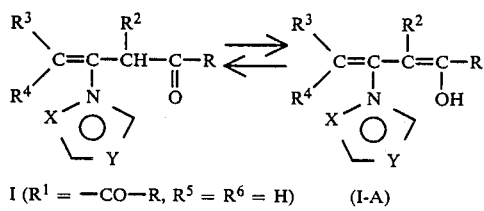

I ($R^1 = -CO-R$, $R^5 = R^6 = H$)   (I-A)

Both heterocyclic compounds of formula II and the unsaturated compounds of formula III are known compounds or they can be easily prepared according to the normal reactions of organic chemistry.

As already mentioned, the compounds of formula I are endowed with phytogrowth regulating activity. The phytogrowth regulating activity is chiefly a dwarfing activity and results in reducing the length of the plant internodes without altering the vital functions. Compounds of formula I have shown a dwarfing activity even better than that of known compounds which are specific for that type of utilization.

The use of dwarfing compounds is essentially directed to reducing the height of some kinds of useful crops in order to reduce the harvest losses due to lodging and to modify the plant structure in favor of flower and fruit development. Among the cultures on which phytogrowth dwarfing compounds can be used, the following may be mentioned:

fruit trees (apple and pear trees), horticultural growths such as tomato, pea and bean and other cultures such as some kinds of cereals and peanuts.

An important field of application is the treatment of ornamental and flower plants.

The compounds of formula I are active both when applied on the leaves and on the ground where the plant grows. In practice, the phytogrowth regulators of formula I may be used as such or preferably in the form of suitable formulations.

Normally, for these applications, liquid formulations are preferred, they can be diluted in water and used to spray the plants or to water the ground, and the formulations in powder or as wettable powder. Generally the formulations contain, in addition to the active substance (compound of formula I), an inert liquid vehicle (water, organic solvent, oil) or an inert solid vehicle (talc, bentonite, kaolin calcium carbonate, etc.), and optionally other additives like surfactants, wetting agents, suspending agents, sticking agents, etc.

The amount of active substance to be distributed varies over wide ranges, as a function of different factors such as the type of cultivation, treatment on the leaves or on the ground, the type of composition, the available applicative means, the place (open field or greenhouse), the specific effectiveness of the compound also as a function of the abovementioned factors, climatic and environmental conditions.

Generally amounts of the compound of formula I comprised between 0.1 and 10 kg/ha, or between 1 and 100 mg each plant, are sufficient to obtain the desired results.

We have also observed that, in higher doses, compounds of formula I also possess herbicidal activity. This activity is evident, both in pre-emergence and in post-emergence treatments, against several weeds which infest useful crops, especially against dicotyledonous weeds.

The following examples are given to illustrate the invention in more detail and are not limiting.

EXAMPLE 1

Preparation of the methyl ester of 2-acetyl-3-(1-imidazolyl)-4,4-dichloro-3-butenoic acid (compound No. 2).

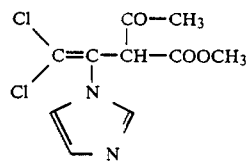

13 g of methyl ester of 2-acetyl-4,4,4-trichloro-2-butenoic acid

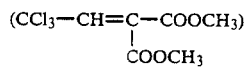

at 35% concentration were added dropwise to a solution containing 3.4 g of imidazole in 39 ml of triethylamine maintained under stirring at room temperature. Since the reaction is exothermic, the addition is regulated in such way that the temperature does not exceed 30° C.

On completion of the addition, the reaction mixture was maintained under stirring for 6 hours at room temperature. The triethylamine was removed by evaporation at reduced pressure and the residue was diluted with 150 ml of chloroform.

The organic solution was washed with water (2×20 ml) and dried on anhydrous Na₂SO₄. The solvent was removed by evaporation at reduced pressure and the residue was purified by chromatography on silica gel (eluent n-hexane-ethyl acetate in 8:2 ratio). 2.8 g of the desired product were obtained as a liquid at room temperature.

Elemental analysis (rough formula C₁₀H₁₀Cl₂N₂O₃): Calculated: C=43.34%; H=3.64%; N=10.11%; Cl=25.60%. Found: C=44.02%; H=3.77%; N=10.04%; Cl=25.64%.

IR: consistent with the assigned structure.

¹H—NMR (CDCl₃, TMS)

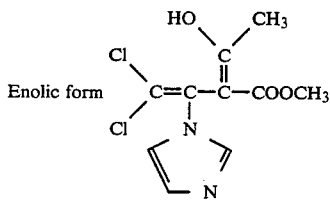

Enolic form

δ (ppm): 2.1 (s, 3H, CH₃—C); 3.72 (s, 3H, COOCH₃); 6.94 (s, 1H, heterocyclic CH); 7.08 (s, 1H, heterocyclic CH); 7.6 (s, 1H, heterocyclic CH); 13.08 (s,1H, OH); (s=singlet).

EXAMPLE 2

Preparation of methyl ester of 2-acetyl-3[1-(1,2,4-triazolyl)]-4,4,4-trichlorobutenoic acid (compound of formula IV)

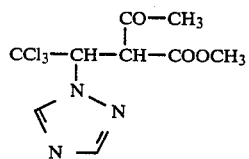

A solution containing 3.45 g of 1,2,4-triazole, 13 g of methyl ester of 2-acetyl-4,4,4-trichloro-2-butenoic acid (pure at 95%) and 0.2 g of KOH in 100 ml of dimethylformamide, was heated under stirring for 10 hours at 50° C.

The solvent was then removed by evaporation at reduced pressure and the residue was diluted with 150 ml of chloroform. The organic solution was washed with water (2×20 ml) and dried on anhydrous Na₂SO₄.

The solvent was removed by evaporation at reduced pressure and the crude product, washed in acetone, afforded 6 g of the desired product in the form of a crystalline solid (m.p.=120°–121° C.).

Elemental analysis (rough formula C₉H₁₀Cl₃N₃O₃): Calculated: C=34.36%; H=3.20%; N=13.36%; Cl=33.82%. Found: C=34.87%; H=3.19%; N=13.40%; Cl=34.00%.

IR: consistent with the assigned structure

¹H-NMR (CDCl₃, TMS) δ (ppm): 2.46 (s, 3H, CH₃—CO); 3.51 (s, 3H, COOCH₃; 4.88 (d, 1H, $$-\overset{|}{\underset{|}{CH}},$$

J=9 Hz); 6.00 (d, 1H, $$-\overset{|}{\underset{|}{CH}},$$

J=9 Hz); 7.96 (s, 1H, heterocyclic CH); 8.44 (s, 1H, heterocyclic CH);
(s=singlet, d=doublet, J=coupling constant).

EXAMPLE 3

Preparation of methyl ester of 2-acetyl-3[1-(1,2,4-triazolyl)]-4,4-dichloro-3-butenoic acid (compound No. 1)

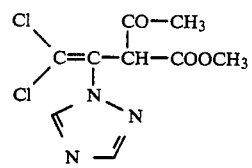

The compound was prepared from 1,2,4-triazole and from methyl ester of 2-acetyl-4,4,4-trichloro-2-butenoic acid by a procedure analogous to that of Example 1. The compound was liquid at room temperature.

IR: consistent with the assigned structure.

¹H—NMR (CDCl₃, TMS)

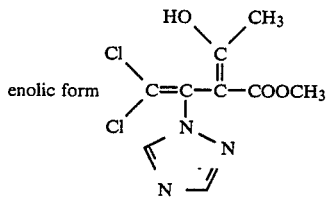

enolic form

δ (ppm): 2.21 (s, 3H, CH₃—C); 3.71 (s, 3H, COOCH₃); 8.10 (s, 1H, heteroeocyclic CH); 8.43 (s, 1H, heterocyclic CH); 13.03 (s, 1H, OH).
(s=singlet)

The preparation of the title compound was also carried out starting from the formula IV compound described in Example 2 by treatment with triethylamine.

After work-up of the reaction mixture the desired compound was obtained having the same spectroscopic characteristics as those hereabove reported.

EXAMPLE 4

By operating analogously to Example 2, the following intermediate compounds of formula IV have been prepared:
methyl ester of 2-acetyl-3-[1-(1,2,4-triazolyl)]-4,4,4-trichloro-butenoic acid (m.p.=120°–121° C.);
1,1,1-trichloro-2-[1-(1,2,4-triazolyl)]-3-acetylpentan-4-one (m.p.=117°–119° C.);
ethyl ester of 2-acetyl-3-[1-(1,2,4-triazolyl)]-4,4,4-trichloro-butenoic acid (m.p.=76°–78° C.);
ethyl ester of 2-ethoxycarbonyl-3-[1-(1,2,4-triazolyl)]-4,4,4-trichloro-butenoic acid (m.p.=73°–75° C.);
methyl ester of 2-methoxycarbonyl-3-[1-(1,2,4-triazolyl)]-4,4,4-trichloro-butenoic acid (m.p.=132°–134° C.).

The elemental analysis and the data of the IR and NMR spectroscopy examinations of the said compounds were consistent with the assigned structures.

By dehydrogehalogenation, these compounds afford the corresponding compounds of formula I.

EXAMPLE 5

Compounds of the invention, prepared according to the procedure described in Example 1, are reported in the following Table 1.

TABLE 1

Compounds of formula[a]

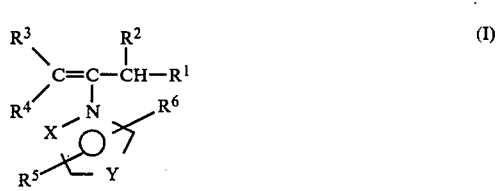

| Compound No. | R[1] | R[2] | R[3] | R[4] | R[5] | R[6] | X | Y | Physical state at room temperature |
|---|---|---|---|---|---|---|---|---|---|
| 1[b] | COOCH$_3$ | CO—CH$_3$ | Cl | Cl | H | H | N | N | yellow oil |
| 2[c] | COOCH$_3$ | CO—CH$_3$ | Cl | Cl | H | H | CH | N | yellow oil |
| 3 | CO—CH$_3$ | CO—CH$_3$ | Cl | Cl | H | H | N | N | red oil |
| 4 | CO—CH$_3$ | CO—CH$_3$ | Cl | Cl | H | H | CH | N | solid (m.p. = 95–97° C.) |
| 5 | COOC$_2$H$_5$ | CO—CH$_3$ | Cl | Cl | H | H | N | N | solid (m.p. = 66–68° C.) |
| 6 | COOC$_2$H$_5$ | CO—CH$_3$ | Cl | Cl | H | H | CH | N | solid (m.p. = 65–66° C.) |
| 7 | COOC$_2$H$_5$ | COOC$_2$H$_5$ | Cl | Cl | H | H | N | N | semisolid, waxy |
| 8 | COOC$_2$H$_5$ | COOC$_2$H$_5$ | Cl | Cl | H | H | CH | N | yellow oil |
| 9 | COOCH$_3$ | COOCH$_3$ | Cl | Cl | H | H | N | N | solid (m.p. = 93–95° C.) |

Notes to Table 1:
[a]The elemental analysis and the IR and NMR spectroscopy data of all the compounds were consistent with the assigned structure.
[b]The preparation is described in Example 3.
[c]The preparation is described in Example 1.

EXAMPLE 6

Determination of the phytogrowth regulating activity.

Dwarfing activity on bean by application on the leaves.

General methodology: small bean plants c.v. "Borlotto di Vigevano" grown in pots having a diameter of 11 cm, at a development stage of two cotyledon leaves, were sprinkled with a hydroacetonic solution (20% by vol. of acetone) containing a wetting agent and the products under examination at a concentration of 0.3 and 0.1% by weight.

The plants were kept in a conditioned environment at 21° C. with a photoperiod of 16 hours of light for 14 days. As a control, the same operations were carried out on another set of small bean plants, but by sprinkling only with the hydroacetonic solution and the wetting agent, without any active product.

At the end of this period the stalk lengthening was measured to the fourth foliar layer. The data of phytogrowth dwarfing activity were obtained by comparing the stalk length of the treated plants with that of non-treated plants, by considering the average lengthening of these latter as 100.

The results obtained with compounds according to the invention, compared with two known compounds used as dwarfing agents, are recorded in Table 2.

TABLE 2

Dwarfing activity on bean plants by application on leaves

| Compound | Concentration (%) | Average lengthening referred to the control (%) |
|---|---|---|
| Control | — | 100 |
| Daminozide[a] | 0.3 | 7 |
|  | 0.1 | 9 |
| Chlormequat[b] chloride | 0.3 | 12 |
|  | 0.1 | 16 |
| 1[c] | 0.3 | 14 |
|  | 0.1 | 21 |
| 2[c] | 0.3 | 9 |
|  | 0.1 | 16 |

Notes for Table 2
[a]Daminozide = common name of the compound succinic acid dimethylhydrazide having the formula

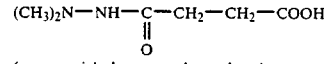

(commercial phytogrowth regulator).
[b]Chlormequat chloride = common name of the compound 2-chloroethyl-trimethylammonium chloride having the formula

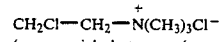

(commercial phytogrowth regulator).
[c]Compounds No. 1 and 2 are reported in Table 1.

EXAMPLE 7

Determination of the phytogrowth regulating activity.

Dwarfing activity on bean by radical application.

General methodology: small bean plants grown in pots having diameter of 11 cm and containing glasshouse loam, at a development stage of two cotyledon leaves, were watered on the ground with 50 ml each pot of an aqueous solution at 0.25% of DMSO containing 10 or 2.5 mg of the product under examination. As a control another set of small bean plants was watered on the ground with 50 ml of an aqueous solution of DMSO (0.25%) without any active product.

The plants were kept in a conditioned environment at 21° C. with photoperiod of 16 hours of light for 14 days. At the end of this period the dwarfing activity was determined as described in Example 6. The results are recorded in the following Table 3.

TABLE 3

Dwarfing activity on bean plants by radical application

| Compound No. (see Table 1) | Dose (mg/pot) | Average lengthening referred to the control (%) |
|---|---|---|
| Control | — | 100 |
| Daminozide[a] | 10 | 82 |
|  | 5 | 93 |
|  | 2.5 | 95 |
| Chlormequat[b] Chloride | 10 | 68 |
|  | 5 | 74 |
|  | 2.5 | 74 |
| 1 | 10 | 24 |
|  | 5 | 36 |
|  | 2.5 | 46 |
| 2 | 10 | 29 |
|  | 5 | 47 |
|  | 2.5 | 49 |
| 3 | 10 | 14 |
| 4 | 10 | 24 |
| 5 | 10 | 16 |
| 6 | 10 | 17 |

Notes for Table 3
[a]Daminozide = succinic acid dimethylhydrazide
[b]Chlormequat chloride = 2 chloroethyl-trimethylammonium chloride.

EXAMPLE 8

Determination of the phytogrowth regulating activity.

Dwarfing activity on Tagetes by radical application.

General methodology: small tagetes plants (height=10 cm), grown in pots having a diameter of 11 cm and containing glasshouse loam were watered on the ground with 50 ml of an aqueous solution of DMSO at 0.25% containing 25 or 10 mg of the compound under examination. As a control, another analogous set of small plants was watered on the ground with an aqueous solution of DMSO at 0.25% without any active product. Then the plants were transferred to the glasshouse and kept at 16°–26° C. with 12 hours of lighting per day.

After 7 and 14 days, the height of the plants was measured. The dwarfing activity of the compounds under examination was determined by comparing the average lengthening of the small plants treated with each compound in comparison with the average lengthening of the control plants, by considering the latter as 100. The results are recorded in the following Table 4.

TABLE 4

Dwarfing activity on Tagetes plants by radical application

| Compound | Dose (mg/pot) | Average lengthening referred to the control (%) After 7 days | After 14 days |
|---|---|---|---|
| Control | — | 100 | 100 |
| Daminozide[a] | 25 | 87 | 87 |
|  | 10 | 112 | 113 |
| Chlormequat[b] chloride | 25 | 75 | 87 |
|  | 10 | 75 | 93 |
| 2 | 25 | 25 | 47 |

TABLE 4-continued

Dwarfing activity on Tagetes plants by radical application

| Compound (see Table 1) | Dose (mg/pot) | Average lengthening referred to the control (%) After 7 days | After 14 days |
|---|---|---|---|
|  | 10 | 37 | 60 |

Notes for Table 4
[a]Daminozide = succinic acid dimethylhydrazide
[b]Chlormequat chloride = 2 chloroethyl-trimethylammonium chloride

EXAMPLE 9

Determination of the phytogrowth regulating activity.

Activity inhibiting the lengthening of lettuce hypocotyl promoted by gibberellic acid ($GA_3$).

The test was carried out to verify the antagonism between the action of the natural hormone (gibberellic acid) and the products of the invention.

General methodology: lettuce seeds had been allowed to germinate in Petri dishes at 15° C. for three days in the dark. The seeds were then transferred to Petri dishes (10 seeds each dish) containing 5 ml of an aqueous solution at 1% of DMSO, where the products under examination at a $10^{-4}$ molar concentration and gibberellic acid at a $10^{-5}$ molar concentration were dissolved.

As a control, a set of germinated seeds were transferred to Petri dishes containing analogous solutions of gibberellic acid without the dwarfing compound and another set was transferred to Petri dishes containing only an aqueous solution of DMSO at 1% without any other compound. Then the Petri dishes were exposed to fluorescent light at a temperature of 25° C.

The results were determined by comparing the hypocotyl lengthening of the treated plants in comparison with that of the plants treated only with gibberellic acid and by considering this last value as 100 (control in the absence of gibberellic acid=0).

TABLE 5

Dwarfing activity in antagonism to gibberellic acid on lettuce plants

| Active compounds[a] (molar concentration) | Average lengthening referred to the control (%) |
|---|---|
| Control without $GA_3$ | 0 |
| $GA_3$ ($10^{-5}$) control | 100 |
| $GA_3$ ($10^{-5}$) + Daminozide ($10^{-4}$) | 109 |
| $GA_3$ ($10^{-5}$) + No. 1 ($10^{-4}$) | 47 |
| $GA_3$ ($10^{-5}$) + No. 2 ($10^{-4}$) | 23 |
| $GA_3$ ($10^{-5}$) + No. 5 ($10^{-4}$) | 34 |
| $GA_3$ ($10^{-5}$) + No. 6 ($10^{-4}$) | 49 |

Notes for Table 5
[a]$GA_3$ gibberellic acid (natural hormone).
Daminozide = succinic acid dimethylhydrazyde (known dwarfing agent).
Compounds No. 1, 2, 5 and 6 are reported in Table 1.

We claim:
1. A compound of formula

$$\begin{array}{c} R^3 \\ \phantom{R}\diagdown \\ R^4 \diagup \end{array} C = C \begin{array}{c} R^2 \\ | \\ -CH-R^1 \end{array} \quad (I)$$

in which $R^1$ and $R^2$, the same or different are;

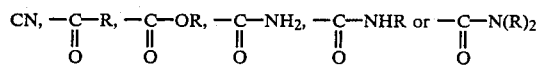

wherein R is a $C_1$–$C_4$ alkyl;

$R^3$ and $R^4$, the same or different, are a chlorine or bromine atom;

$R^5$ and $R^6$, the same or different, are a hydrogen atom or a $C_1$–$C_5$ alkyl;

X is a nitrogen atom or a CH group.

2. A compound according to claim 1, in which $R^1$ and $R^2$, the same or different, are a

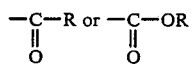

group and R is a $C_1$–$C_4$ alkyl.

3. A compound according to claim 2, in which X is a CH group.

4. A compound according to claim 2, in which X is a nitrogen atom.

5. A process for preparing compounds according to claim 1 characterized in that a heterocyclic compound of formula

in which X, $R^5$ and $R^6$ have the same meaning as in claim 1, is reacted in the presence of an organic or inorganic base, in an inert solvent and at a temperature ranging from room temperature to 60° C., with an unsaturated compound of formula

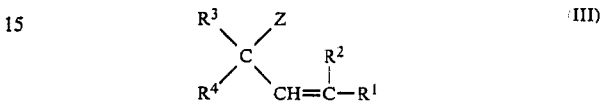

in which $R^1$, $R^2$, $R^3$ and $R^4$ have the same meaning as in claim 1 and Z is Cl or Br.

6. A process, according to claim 5, further characterized in that the reaction is carried out in the presence of an excess of a tertiary amine which serves also as solvent.

7. A process, according to claim 5, further characterized in that the reaction is carried out in the presence of an alkaline hydroxide in a polar solvent.

8. A method of limiting the growth of useful and ornamental plants, without damaging their vital functions, consisting in distributing on the plants or on the soil in which they grow, an effective but not phytotoxic amount of at least one of the compounds of claim 1, as such or in the form of suitable compositions or formulations.

9. Compositions with phytogrowth regulating activity, containing an effective amount of a compound according to claim 1 as active ingredient, an inert solid or liquid vehicle and, optionally, other additives used in the conventional formulation of such compositions.

* * * * *